United States Patent [19]

Schurter et al.

[11] 4,115,100
[45] Sep. 19, 1978

[54] SELECTIVE HERBICIDAL COMPOSITION CONTAINING 2-PYRIDINOL COMPOUNDS

[75] Inventors: Rolf Schurter; Hermann Rempfler, both of Binningen; Werner Föry, Basel, all of Switzerland

[73] Assignee: Ciba-Geigy Corporation, Ardsley, N.Y.

[21] Appl. No.: 772,796

[22] Filed: Feb. 28, 1977

[30] Foreign Application Priority Data

Mar. 5, 1976 [CH] Switzerland ............... 2780/76

[51] Int. Cl.² ............... A01N 9/22; C07D 213/64
[52] U.S. Cl. ............... 71/94; 260/294.8 R; 260/294.8 G; 260/294.9; 260/295 R; 260/293.69; 544/58; 544/131; 542/427; 544/360; 544/399; 544/394
[58] Field of Search ............... 260/294.8 R, 295 R, 260/294.9, 294.8 G; 71/94

[56] References Cited
U.S. PATENT DOCUMENTS 3,609,158  3/1969  Torba ............... 260/295.5 R Primary Examiner—Natalie Trousof
Assistant Examiner—Cary Owens
Attorney, Agent, or Firm—Harry Falber

[57] ABSTRACT

This invention relates to the selective control of weeds and wild grasses in crops of useful plants by means of 2-pyridinol compounds of formula

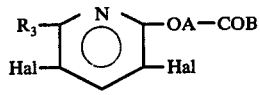

wherein
A is an alkylene or alkenylene bridge
B is a group $-OR_1$ or $-SR_2$,
$R_1$ is alkyl, aralkyl, cycloalkyl, alkenyl, alkinyl or phenyl
$R_2$ is alkyl, benzyl or phenyl
$R_3$ is alkyl or phenyl and
Hal is chlorine or bromine,
and to compositions therefor.

12 Claims, No Drawings

SELECTIVE HERBICIDAL COMPOSITION CONTAINING 2-PYRIDINOL COMPOUNDS

The present invention relates to a composition for the selective control of weeds and wild grasses in crops of useful plants, which composition contains as active substance novel pyridinol compounds; as well as to the use of this composition.

The novel 2-pyridinol compounds correspond to the formula I

 (I)

wherein
- A represents an alkylene bridge member or alkenylene bridge member each having 1–9 C atoms, which can be branched-chain or straight chain and which can also be substituted by halogen or phenyl or by the groups —COOH or —COOC$_1$—C$_4$alkyl;
- B represents a group —OR$_1$ or —SR$_2$ in which
- R$_1$ represents hydrogen, C$_1$–C$_8$ alkyl which is unsubstituted or substituted by halogen, C$_1$–C$_4$ alkoxy, C$_1$–C$_4$ alkylthio, C$_1$–C$_4$ alkoxycarbonyl, C$_3$–C$_{12}$ cycloalkyl, phenyl which is unsubstituted or mono- or polysubstituted by halogen, C$_1$–C$_4$ alkyl, C$_1$–C$_4$ alkoxy, C$_1$–C$_4$ alkylthio, cyano or nitro, a 5–6 membered heterocyclic radical containing one or two N, O and/or S atoms; C$_3$–C$_{12}$ cycloalkyl; C$_3$–C$_8$ alkenyl which is unsubstituted or substituted by halogen; C$_3$–C$_8$-alkynyl; phenyl which is unsubstituted or mono- or polysubstituted by halogen, C$_1$–C$_4$ alkyl, C$_1$–C$_4$ alkoxy, C$_1$–C$_4$ alkylthio, cyano or nitro; an ion equivalent of an alkali metal atom; or a quaternary C$_1$–C$_4$ alkylammonium group or C$_1$–C$_4$ hydroxyalkyl-ammonium group; and
- R$_2$ represents C$_1$–C$_8$ alkyl, a phenyl or benzyl group which can be unsubstituted or substituted by halogen, C$_1$–C$_4$ alkyl or C$_1$–C$_4$ alkoxy;
- R$_3$ represents C$_1$–C$_4$ alkyl or phenyl; and the
- Hal's independently of one another each represent a chlorine or bromine atom.

In this formula, alkyl groups, also as moiety of alkoxy or alkylthio groups, represent both branched-chain and straight-chain alkyl groups having the given number of carbon atoms. The alkenyl and alkynyl groups R$_1$ or A can be branched-chain or straight-chain and contain the given number of carbon atoms; they preferably represent however allyl, methallyl and propargyl groups. The heterocyclic rings which in the definition of R$_1$ are bound by way of alkyl to the acid group have 5 to 6 ring members and optionally a further hetero atom and are preferably saturated; examples which may be mentioned are the pyrrolidine, piperidine, methylpiperidine, morpholino, thiomorpholino, piperazine, methyl- and phenylpiperazine, tetrahydrofuryl rings, etc.

The alkylene or alkenylene bridge member A can contain up to 9 C atoms; it is preferably methylene, 1- or 2-ethylene or the 2-propylene bridge. The alkenylene bridge member is preferably a vinylene, allylene or methallylene group. These agroups can be substituted by a phenyl group or a C$_1$–C$_4$-alkoxycarbonyl group.

The 2-pyridinol compounds of the formula I are produced by reaction of a 2-pyridinol of the formula II

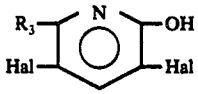 (II), wherein "Hal" and R$_3$ have the given meanings, with a halogen derivative of the formula III

 (III)

wherein "Hal" represents a chlorine or bromine atom, and A and B have the given meanings, in the presence of a basic condensation agent and optionally in a polar solvent. Suitable basic condensation agents are, e.g., NaOH, KOH, alkali metal carbonates or sodium alkanolates.

The 2-pyridinol compounds of the formula I can be produced also by condensing a 2-pyridinol of the formula II with a compound of the formula IV

 (IV)

wherein B has the given meaning, and A' represents a twofold or threefold unsaturated alkenyl or alkynyl having up to 9 carbon atoms.

A' can be an alkenyl group or an alkynylene group, e.g. an ethynyl, propargyl, methylpropargyl, butynyl group, etc.

These condensation reactions are advantageously performed in inert organic solvents at temperatures which can be between room temperature and 250° C. Suitable organic solvents are, e.g., dimethylsulphoxide, acetone, ethyl methyl ketone or some other ketone, acetonitrile, etc.

Compounds of the formula I wherein —COB represents the carboxyl group can be converted by known methods either directly to esters or to thioesters, or by way of the corresponding acid halide. Such conversions of the —COB function are well-known and require no further explanation.

The starting materials of the formula II are in some cases known or can be produced according to the following methods and references:

3,5-Dichloro-6-methylpyridin-2-ol is known; see J. Org. Chem. 23, 1614 (1958), wherein this compound is obtained from 2-hydroxy-6-methyl-pyridine by chlorination in the 3- and 5-position.

Furthermore, such compounds can be obtained by a novel method, whereby trichloroacetic acid nitrile is reacted with alkenyl-aldehydes (e.g. acrolein) or with alkyl-alkenyl ketones (e.g. methyl vinyl ketone), with the addition of suitable radical initiators. The addition product, (2,2,4-trichloropentan-5-one-carboxylic acid nitrile derivative), can be cyclised thermally or under the action of Lewis acids, and subsequently converted by splitting off HCl into the 3,5-dichloropyridinol derivative.

Suitable starting materials of the formula III are acids, esters and thiol esters of halogenated lower fatty acids having 2–5 carbon atoms, e.g. chloro- and bromoacetic acid esters, esters of 2- and 3-chloro- and bromopropionic acid and of the corresponding halogenated further fatty acids. Also the esters of chloro- or bromodicarboxylic acids, such as of 2-bromo-2-methylmalonic acid, 2-chlorosuccinic acid, etc.

Suitable starting materials of the formula IV are, e.g., the esters and thioesters of unsaturated lower fatty acids, such as of acrylic acid, of 3-butenic acid or of crotylic acid, also the esters of unsaturated dicarboxylic acids (alkylidenemalonic acid), such the esters of maleic acid, of fumaric acid and of homologs thereof.

The production of the 3-pyridinol compounds according to the invention is further illustrated in the following Examples. The temperature values are given in degrees Centigrade.

EXAMPLE 1

2-[(3,5-Dichloro-6-methyl)-2-pyridyl)-oxy]-propionic acid ethyl ester 425.4 g (2.39 moles) of 3,5-dichloro-2-hydroxy-6-methylpyridine (see J. Org. Chem. 23, (1958) p. 1614) and 1700 ml of dimethylsulphoxide are placed into a sulphonating flask. To this mixture is slowly added, with ice-cooling and stirring, 138.3 g (2.56 moles) of sodium methylate dissolved in 650 ml of absolute methanol. The methanol is subsequently distilled off under reduced pressure, at 11 mm Hg and at a bath temperature of 70°-80°. To the reaction mixture is subsequently added dropwise at room temperature (20°-30°), with stirring, 525.4 g (2.9 moles) of 2-bromopropionic acid ethyl ester. After this addition is completed, the reaction is performed for a further 2 hours. There is then added to the reaction mixture 1 liter of an ice/water mixture and the whole is extracted three times with 500 ml of ether each time. The combined extracts are washed with saturated sodium chloride solution, dried over magnesium sulphate and finally freed from ether in a rotary evaporator. The oil remaining is distilled under high vacuum at 0.001 mm Hg. The principal part passes over at 112° and solidifies to form a crystalline mass which melts at 36°-37°.

EXAMPLE 2

2-(3,5-Dichloro-6-methyl)-2-pyridyl)-oxy-propionic acid 27.8 g (0.1 mole) of 2-(3,5-dichloro-6-methyl-2-pyridyl)-oxy-propionic acid ethyl ester is refluxed for 1 hour with 150 ml of 2N aqueous sodium hydroxide solution. The solution is then cooled, and concentrated hydrochloric acid is added at room temperature until the pH value has reached 1. A white crystalline mass precipitates; this is washed with water, recrystallised in ethanol/water and dried at 50° C over phosphorus pentoxide in vacuo; yield 24 g; m.p. 149°.

The following substances can be produced analogously to these Examples with further processing of the resulting compounds:

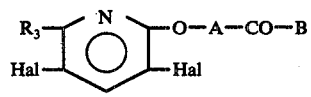

| Comp. No. | $R_3$ | Hal | —A— | B | Physical constants |
|---|---|---|---|---|---|
| 1 | $CH_3$ | Cl | $-CH_2-$ | $-OCH_3$ | m.p. 72° |
| 2 | $CH_3$ | Cl | $-CH_2-$ | $-OC_2H_5$ | m.p. 54-56° |
| 3 | $CH_3$ | Cl | $-C_3H_6-$ | $-OC_2H_5$ | b.p. 124° (0.01 mm Hg) |
| 4 | $CH_3$ | Cl | $-CH(CH_3)-$ | $-OH$ | m.p. 149° |
| 5 | $C_2H_5$ | Cl | $-CH(CH_3)-$ | $-OH$ | m.p. 131-132° |
| 6 | $CH_3$ | Cl | $-CH(CH_3)-$ | $-O^{\ominus}Na^{\oplus}$ | m.p. 222° |
| 7 | $CH_3$ | Br | $-CH(CH_3)-$ | $-O^{\ominus}Na^{\oplus}$ | |
| 8 | $CH_3$ | Cl | $-CH(CH_3)-$ | $-O^{\ominus}K^{\oplus}$ | m.p. 239° |
| 9 | $CH_3$ | Cl | $-CH(CH_3)-$ | $-O^{\ominus}N^{\oplus}H_2(C_2H_4OH)_2$ | m.p. 104-108° |
| 10 | $CH_3$ | Br | $-CH(CH_3)-$ | $-O^{\ominus}N^{\oplus}H_2(C_2H_4OH)_2$ | |
| 11 | $C_2H_5$ | Cl | $-CH(CH_3)-$ | $-O^{\ominus}N^{\oplus}H_3iC_3H_7$ | m.p. 128-129° |
| 12 | $CH_3$ | Cl | $-CH(CH_3)-$ | $-OCH_3$ | m.p. 775-785° |
| 13 | $CH_3$ | Cl | $-CH(CH_3)-$ | $-OC_2H_5$ | m.p. 36-37° |
| 14 | $CH_3$ | Br | $-CH(CH_3)-$ | $-OC_2H_5$ | |
| 15 | $CH_3$ | Cl/Br | $-CH(CH_3)-$ | $-OC_2H_5$ | |
| 16 | $C_2H_5$ | Cl | $-CH(CH_3)-$ | $-OC_2H_5$ | b.p. 110° (0.01 mm Hg) |

-continued $$\underset{\text{Hal}}{\overset{R_3}{\diagup}}\underset{\text{Hal}}{\overset{N}{\bigcirc}}\text{O-A-CO-B}$$

| Comp. No. | $R_3$ | Hal | —A— | B | Physical constants |
|---|---|---|---|---|---|
| 17 | $CH_3$ | Cl | —CH(CH$_3$)— | —SC$_2$H$_5$ | $n_D^{25}$ 1.5472 |
| 18 | C$_6$H$_5$ | Cl | —CH(CH$_3$)— | —OC$_2$H$_5$ | m.p. 74–76° |
| 19 | $CH_3$ | Cl | —CH(CH$_3$)— | —OiC$_3$H$_7$ | $n_D^{25}$ 1.5072 |
| 20 | $CH_3$ | Cl | —CH(CH$_3$)— | —SiC$_3$H$_7$ | b.p. 124° (0.05 mm Hg) |
| 21 | $CH_3$ | Cl | —CH(CH$_3$)— | —OiC$_4$H$_9$ | $n_D^{30}$ 1.5090 |
| 22 | $CH_3$ | Br | —CH(CH$_3$)— | —OiC$_4$H$_9$ | |
| 23 | $CH_3$ | Cl | —CH(CH$_3$)— | —O—CH$_2$(C$_2$H$_5$)$_2$ | m.p. 42–43° |
| 24 | $CH_3$ | Cl | —CH(CH$_3$)— | —S—nC$_7$H$_{15}$ | $n_D^{25}$ 1.5242 |
| 25 | $CH_3$ | Cl | —CH(CH$_3$)— | —OnC$_8$H$_{17}$ | $n_D^{25}$ 1.4945 |
| 26 | $CH_3$ | Cl | —CH(CH$_3$)— | —OCH$_2$—CH=CH$_2$ | $n_D^{25}$ 1.5918 |
| 27 | $CH_3$ | Cl | —CH(CH$_3$)— | —OC$_2$H$_4$C≡CC$_2$H$_5$ | m.p. 37° |
| 28 | $CH_3$ | Br | —CH(CH$_3$)— | —OC$_2$H$_4$C≡CC$_2$H$_5$ | |
| 29 | $CH_3$ | Cl | —CH(CH$_3$)— | —OC$_2$H$_4$Br | m.p. 73–75° |
| 30 | $CH_3$ | Cl | —CH(CH$_3$)— | —OCH$_2$CCl$_3$ | m.p. 76° |
| 31 | $CH_3$ | Cl | —CH(CH$_3$)— | —OC$_6$H$_{12}$Cl | $n_D^{27}$ 1.5100 |
| 32 | $CH_3$ | Cl | —CH(CH$_3$)— | OC$_2$H$_4$OCH$_3$ | $n_D^{27}$ 1.5092 |
| 33 | $CH_3$ | Cl | —CH(CH$_3$)— | OC$_2$H$_4$SC$_2$H$_5$ | |
| 34 | $CH_3$ | Cl | —CH(CH$_3$)— | OC$_2$H$_4$OnC$_4$H$_9$ | $n_D^{27}$ 1.4980 |
| 35 | $CH_3$ | Br | —CH(CH$_3$)— | OC$_2$H$_4$OnC$_4$H$_9$ | |
| 36 | $CH_3$ | Cl | —CH(CH$_3$)— | O—CH(CH$_3$)—COOCH$_3$ | |
| 37 | $CH_3$ | Cl | —CH(CH$_3$)— | OCH$_2$—C$_6$H$_5$ | m.p. 60–62° |
| 38 | $CH_3$ | Cl | —CH(CH$_3$)— | O—CH$_2$—C$_6$H$_4$—Cl | m.p. 78° |
| 39 | $CH_3$ | Cl | —CH(CH$_3$)— | O—C$_3$H$_6$—C$_6$H$_5$ | $n_D^{25}$ 1.5430 |
| 40 | $CH_3$ | Cl | —CH(CH$_3$)— | OCH$_2$-(tetrahydrofuryl) | $n_D^{27}$ 1.5205 |

-continued $$R_3 - \underset{Hal}{\underset{|}{\bigcirc}} \overset{N}{\underset{Hal}{\overset{|}{\bigcirc}}} - O-A-CO-B$$

| Comp. No. | $R_3$ | Hal | —A— | B | Physical constants |
|---|---|---|---|---|---|
| 41 | CH₃ | Br | —CH—<br>\|<br>CH₃ | OCH₂—⟨O⟩ (tetrahydrofuryl) | |
| 42 | CH₃ | Cl | —CH—<br>\|<br>CH₃ | O—⟨H⟩ | $n_D^{25}$ 1.5172 |
| 43 | CH₃ | Br | —CH—<br>\|<br>CH₃ | O—⟨H⟩ | |
| 44 | CH₃ | Cl | —CH—<br>\|<br>CH₃ | O—⟨○⟩ | m.p. 66–68° |
| 45 | CH₃ | Cl | —CH—<br>\|<br>CH₃ | S—⟨○⟩ | $n_D^{25}$ 1.5935 |
| 46 | CH₃ | Cl | —CH—<br>\|<br>CH₃ | O—⟨○⟩—OCH₃ | m.p. 90–93° |
| 47 | CH₃ | Cl | —CH—<br>\|<br>C₂H₅ | OC₂H₅ | b.p. 100–103° |
| 48 | CH₃ | Br | —CH—<br>\|<br>C₂H₅ | OC₂H₅ | |
| 49 | CH₃ | Cl | —CH—<br>\|<br>iC₃H₇ | OC₂H₅ | b.p. 95–98° (0.01 mm Hg) |
| 50 | CH₃ | Cl | —CH—<br>\|<br>nC₈H₁₇ | OH | m.p. 87–89° |
| 51 | CH₃ | Cl | —CH—<br>\|<br>nC₈H₁₇ | OC₂H₅ | b.p. 138(0.01 mm Hg) |
| 52 | CH₃ | Cl | —CH—<br>\|<br>COOH | OH | m.p. 167° |
| 53 | CH₃ | Cl | —CH—<br>\|<br>COOC₂H₅ | OC₂H₅ | m.p. 39–41° |

The herbicidal activity of the compounds of the formula I was examined by means of the following tests:

EXAMPLE 3

Pre-emergence process

Plant seeds were sown in a greenhouse in pots of 12–15 cm diameter, so that about 8–20 plants could develop in each pot. One day after sowing, the pots were sprayed with a spray liquor of the substance to be tested; spraying was performed in such a manner that the amount of active substance applied corresponded to an applied concentration in the field of 4, 2, 1 and 0.5 kg per hectare. The pots were then left in the greenhouse under optimum conditions, i.e. 50–70% humidity, at a temperature of 20°–23° C with regular watering. The test was evaluated after 20 days, and the condition of the plants was assessed according to the following scale of values:

1 plant thrives normally in the same way as the control plant,
2–3 slight damage,
4–6 moderate permanent damage,
7–8 severe irreversible damage,
9 plant destroyed,
– plant or corresponding concentration not tested.

Post-emergence Process

The plant seeds were sown in pots and were allowed to germinate and to develop to the stage at which the young plants had 3 true leaves, a process which took about 12 days. The pots were then treated with a spray liquor containing the test substance in such a manner that a concentration of active substance was applied which was equivalent to an applied concentration in the field of 4, 2, 1 and 0.5 kg per hectare. The pots were then kept in the greenhouse under optimum conditions and the test was evaluated 15 days after the application of the test substance. The plants were assessed on the basis of the scale of values given in the foregoing.

The spray liquor was a 1% dispersion which had been obtained from a 25% wettable powder diluted with water.

The tested compounds exhibited in this test good herbicidal properties both against monocotyledons and, in particular, against dicotyledons, with the useful plants, wheat, barley and rice, remaining unharmed in the post-emergence process.

The results are summarised in the following Table. The comparison compound concomitantly tested was 4-amino-3,5,6-trichloropicolinic acid (A), known from Science 141, 363 (1963) or from U.S. Pat. No. 3,234,229.

-continued

Pre-emergence test

| Compound No. | 6 | | | | 9 | | | | 13 | | | | 21 | | | | 27 | | | | 34 | | | | 40 | | | |
|---|---|---|---|---|---|---|---|---|---|---|---|---|---|---|---|---|---|---|---|---|---|---|---|---|---|---|---|---|
| Amount applied kg/hectare | 4 | 2 | 1 | ½ | 4 | 2 | 1 | ½ | 4 | 2 | 1 | ½ | 4 | 2 | 1 | ½ | 4 | 2 | 1 | ½ | 4 | 2 | 1 | ½ | 4 | 2 | 1 | ½ |
| plant | | | | | | | | | | | | | | | | | | | | | | | | | | | | |
| barley | 1 | 1 | 2 | 2 | 2 | 3 | 7 | 9 | 4 | 7 | 9 | 9 | 2 | 3 | 9 | 9 | 1 | 3 | 6 | 8 | 2 | 3 | 5 | 8 | 2 | 4 | 5 | 9 |
| wheat | 2 | 2 | 3 | 5 | 2 | 3 | 5 | 8 | 6 | 8 | 9 | 9 | 6 | 9 | 9 | 9 | 2 | 2 | 4 | 7 | 3 | 5 | 7 | 8 | 4 | 4 | 7 | 8 |
| maize | 1 | 2 | 3 | 4 | 2 | 4 | 6 | 7 | 2 | 5 | 5 | 9 | 3 | 7 | 9 | 9 | 2 | 2 | 4 | 4 | 2 | 3 | 3 | 6 | 3 | 3 | 4 | 7 |
| millet | 1 | 2 | 2 | 3 | 1 | 2 | 2 | 4 | 2 | 3 | 6 | 8 | 3 | 8 | 9 | 9 | 2 | 2 | 3 | 3 | 2 | 3 | 3 | 3 | 2 | 3 | 3 | 6 |
| rice | 1 | 1 | 2 | 2 | 1 | 1 | 2 | 2 | 1 | 1 | 2 | 2 | 2 | 2 | 2 | 6 | 1 | 1 | 2 | 2 | 1 | 1 | 1 | 2 | 1 | 2 | 2 | 2 |
| soya bean | 1 | 2 | 2 | 2 | 1 | 1 | 3 | 6 | 2 | 4 | 5 | 7 | 2 | 2 | 7 | 9 | 1 | 1 | 2 | 6 | 1 | 2 | 2 | 4 | 1 | 1 | 3 | 5 |
| cotton | 2 | 3 | 3 | 3 | 1 | 2 | 3 | 6 | 3 | 4 | 7 | 9 | 4 | 4 | 8 | 9 | 3 | 3 | 3 | 9 | 2 | 2 | 3 | 4 | 2 | 2 | 4 | 7 |
| avena fatua | 3 | 3 | 3 | 3 | 3 | 3 | 5 | 7 | 5 | 7 | 9 | 9 | 2 | 3 | 8 | 9 | 2 | 2 | 6 | 9 | 2 | 4 | 4 | 7 | 2 | 3 | 6 | 7 |
| lolium perenne | 2 | 3 | 6 | 7 | 4 | 4 | 8 | 9 | 9 | 9 | 9 | 9 | 3 | 9 | 9 | 9 | 2 | 4 | 7 | 9 | 2 | 5 | 8 | 9 | 4 | 6 | 7 | 9 |
| alopecurus myosuroides | 3 | 2 | 4 | 6 | 2 | 2 | 3 | 6 | 2 | 6 | 7 | 9 | 3 | 6 | 9 | 9 | 1 | 1 | 2 | 3 | 1 | 3 | 6 | 9 | 2 | 4 | 5 | 8 |
| bromus tectorum | 2 | 2 | 3 | 4 | 1 | 2 | 2 | 4 | — | — | — | — | 3 | 4 | 6 | 9 | 1 | 2 | 2 | 4 | 1 | 2 | 3 | 4 | 2 | 2 | 5 | 5 |
| cyperus esculentus | 1 | 2 | 7 | 9 | 2 | 4 | 8 | 9 | 7 | — | 9 | — | 6 | 9 | 9 | 9 | 1 | 4 | 8 | 9 | 2 | 3 | 7 | 8 | 2 | 3 | 8 | 9 |
| rottboellia exaltata | 1 | 1 | 2 | 2 | 1 | 2 | 2 | 5 | 2 | 2 | 3 | 7 | 1 | 2 | 8 | 9 | 1 | 1 | 3 | 6 | 1 | 2 | 3 | 4 | 1 | 2 | 4 | 5 |
| digitaria sanguinalis | 1 | 2 | 2 | 2 | 1 | 1 | 1 | 2 | 1 | 1 | 1 | 3 | 1 | 1 | 2 | 3 | 1 | 1 | 1 | 2 | 1 | 1 | 1 | 2 | 1 | 1 | 1 | 3 |
| setaria italica | 1 | 2 | 2 | 2 | 1 | 2 | 2 | 7 | 2 | 4 | 6 | 9 | 4 | 6 | 9 | 9 | 1 | 2 | 2 | 4 | 1 | 1 | 2 | 3 | 1 | 1 | 3 | 4 |
| echinochloa crus galli | 1 | 2 | 2 | 2 | 1 | 1 | 2 | 5 | 2 | 2 | 4 | 8 | 2 | 2 | 8 | 9 | 1 | 2 | 2 | 2 | 2 | 2 | 2 | 3 | 1 | 2 | 2 | 4 |
| beta vulgaris | 1 | 1 | 1 | 1 | 1 | 1 | 1 | 1 | 1 | 1 | 2 | 2 | 1 | 1 | 2 | 2 | 1 | 1 | 1 | 1 | 1 | 1 | 2 | 1 | 1 | 1 | 1 | 1 |
| sesbania exaltata | 1 | 1 | 1 | 1 | 1 | 1 | 1 | 1 | 1 | 2 | 2 | 7 | 1 | 1 | 1 | 3 | 1 | 1 | 1 | 1 | 1 | 1 | 1 | 1 | 1 | 1 | 1 | 1 |
| amaranthus retroflexus | 1 | 1 | 1 | 1 | 1 | 1 | 1 | 1 | 1 | 1 | 1 | 1 | 2 | 2 | 2 | 1 | 1 | 1 | 1 | 1 | 1 | 1 | 1 | 1 | 1 | 1 | 1 | 2 |
| sinapis alba | 1 | 1 | 1 | 1 | 1 | 1 | 1 | 1 | 1 | 2 | 2 | 3 | 1 | 1 | 4 | 9 | 1 | 1 | 2 | 2 | 1 | 1 | 1 | 1 | 1 | 1 | 1 | 2 |
| ipomoea purpurea | 1 | 1 | 1 | 1 | 1 | 1 | 1 | 2 | 1 | 1 | 1 | 4 | 1 | 1 | 7 | 9 | 1 | 1 | 1 | 1 | 1 | 1 | 1 | 1 | 1 | 1 | 1 | 2 |
| galium aparine | 1 | 1 | 1 | 1 | 1 | 1 | 1 | 1 | 1 | 1 | 2 | 3 | 1 | 1 | 1 | 1 | 1 | 1 | 1 | 1 | 1 | 1 | 1 | 1 | 1 | 1 | 1 | 1 |
| pastinaca sativa | 1 | 2 | 2 | 3 | 2 | 3 | 5 | 7 | 3 | 5 | 6 | 9 | 2 | 3 | 9 | 9 | 2 | 2 | 2 | 2 | 1 | 2 | 2 | 6 | 1 | 2 | 4 | 7 |
| sida spinosa | 1 | 1 | 2 | 2 | 1 | 1 | 1 | 2 | 2 | 3 | 3 | 3 | 1 | 3 | 4 | 4 | 1 | 2 | 2 | 2 | 1 | 1 | 2 | 2 | 1 | 1 | 1 | 3 |
| rumex sp. | — | — | — | — | — | — | — | — | — | — | — | — | — | — | — | — | — | — | — | — | 1 | 1 | 1 | 1 | 1 | 1 | 1 | 2 |
| chrysanthemum leucum | 1 | 1 | 1 | 2 | 1 | 2 | 2 | 4 | 1 | 2 | 4 | 7 | 1 | 6 | 8 | 9 | 1 | 1 | 2 | 4 | 1 | 2 | 2 | 5 | 1 | 1 | 3 | 6 |
| abutilon sp. | 1 | 1 | 1 | 1 | 1 | 1 | 1 | 2 | — | — | — | — | 1 | 3 | 5 | 6 | 1 | 1 | 3 | 3 | 1 | 1 | 2 | 5 | 1 | 1 | 4 | 4 |
| solanum nigrum | 1 | | 1 | 1 | 1 | 1 | 1 | 2 | — | — | — | — | 1 | 4 | 4 | 6 | 1 | 1 | 1 | 2 | 1 | 1 | 1 | 8 | 1 | 1 | 1 | 1 |

Pre-emergence test

| Compound No. | 42 | | | | A | | | |
|---|---|---|---|---|---|---|---|---|
| Amount applied kg/hectare | 4 | 2 | 1 | ½ | 4 | 2 | 1 | ½ |
| plant | | | | | | | | |
| barley | 5 | 8 | 9 | 9 | 2 | 2 | 8 | 9 |
| wheat | 6 | 8 | 9 | 9 | 1 | 2 | 3 | 4 |
| maize | 3 | 4 | 7 | 7 | 2 | 2 | 3 | 5 |
| millet | 2 | 3 | 6 | 6 | 1 | 1 | 1 | 1 |
| rice | 1 | 1 | 2 | 2 | 1 | 1 | 2 | 3 |
| soya bean | 3 | 3 | 6 | 7 | 1 | 1 | 1 | 1 |
| cotton | 2 | 6 | 8 | 9 | 1 | 1 | 1 | 1 |
| avena fatua | 3 | 5 | 7 | 9 | — | — | — | — |
| lolium perenne | 4 | 4 | 7 | 9 | 2 | 7 | 8 | 9 |
| alopecurus myosuroides | 2 | 3 | 5 | 9 | 1 | 1 | 2 | 3 |
| bromus tectorum | 2 | 3 | 6 | 9 | — | — | — | — |
| cyperus esculentus | 3 | 8 | 9 | 9 | — | — | — | — |
| rottboellia exaltata | 3 | 3 | 6 | 9 | — | — | — | — |
| digitaria sanguinalis | 1 | 1 | 1 | 2 | 1 | 1 | 1 | 1 |
| setaria italica | 1 | 2 | 5 | 7 | 1 | 1 | 1 | 1 |
| echinochloa crus galli | 1 | 2 | 2 | 4 | 1 | 1 | 3 | 7 |
| beta vulgaris | 1 | 1 | 2 | 6 | 1 | 1 | 1 | 1 |
| sesbania exaltata | 1 | 1 | 1 | 4 | — | — | — | — |
| amaranthus retroflexus | 1 | 1 | 1 | 2 | 1 | 1 | 1 | 1 |
| sinapis alba | 1 | 1 | 2 | 5 | 2 | 2 | 3 | 3 |
| ipomoea purpurea | 1 | 1 | 1 | 4 | 1 | 1 | 1 | 1 |
| galium aparine | 1 | 1 | 1 | 1 | 1 | 1 | 1 | 1 |
| pastinaca sativa | 2 | 3 | 4 | 7 | 1 | 1 | 1 | 1 |
| sida spinosa | 1 | 1 | 2 | 3 | — | — | — | — |
| rumex sp. | 1 | 1 | 1 | 2 | — | — | — | — |
| chrysanthemum leucum | 1 | 1 | 5 | 6 | 1 | 1 | 1 | 1 |
| abutilon sp. | 1 | 2 | 7 | 7 | — | — | — | — |
| solanum nigrum | 1 | 1 | 2 | 7 | — | — | — | — |

Post-emergence test

| Compound No. | 6 | | | | 9 | | | | 13 | | | | 21 | | | | 27 | | | |
|---|---|---|---|---|---|---|---|---|---|---|---|---|---|---|---|---|---|---|---|---|
| Amount applied kg/hectare | 4 | 2 | 1 | ½ | 4 | 2 | 1 | ½ | 4 | 2 | 1 | ½ | 4 | 2 | 1 | ½ | 2 | 4 | 1 | 1 |
| plant | | | | | | | | | | | | | | | | | | | | |
| barley | 7 | 8 | 9 | 9 | 9 | 9 | 9 | 9 | 8 | 9 | 9 | 9 | 8 | 9 | 9 | 9 | 8 | 8 | 9 | 9 |
| wheat | 8 | 8 | 9 | 9 | 9 | 9 | 9 | 9 | 9 | 9 | 9 | 9 | 8 | 9 | 9 | 9 | 7 | 8 | 9 | 9 |
| maize | 2 | 6 | 8 | 8 | 3 | 9 | 9 | 9 | 6 | 7 | 7 | 8 | 7 | 9 | 9 | 9 | 7 | 7 | 9 | 9 |
| millet | 3 | 3 | 7 | 9 | 4 | 6 | 6 | 8 | 9 | 9 | 9 | 8 | 8 | 9 | 9 | 9 | 7 | 4 | 5 | 6 |
| rice | 4 | 4 | 8 | 9 | 6 | 6 | 7 | 7 | 7 | 8 | 9 | 9 | 7 | 7 | 9 | 9 | 6 | 7 | 9 | 9 |
| soya bean | 2 | 2 | 2 | 3 | 2 | 2 | 2 | 3 | 2 | 3 | 4 | 6 | 2 | 3 | 3 | 4 | 2 | 2 | 3 | 3 |
| cotton | 2 | 3 | 4 | 4 | 3 | 3 | 4 | 4 | 3 | 3 | 3 | 6 | 2 | 3 | 6 | 7 | 2 | 2 | 3 | 3 |

-continued

| | | | | | | | | | | | | | | | | | | | | |
|---|---|---|---|---|---|---|---|---|---|---|---|---|---|---|---|---|---|---|---|---|
| avena fatua | 6 | 8 | 9 | 9 | 7 | 9 | 9 | 9 | 8 | 9 | 9 | 9 | 9 | 9 | 9 | 9 | 8 | 8 | 9 | 9 |
| lolium perenne | 8 | 8 | 9 | 9 | 7 | 7 | 9 | 9 | 9 | 9 | 9 | 9 | 7 | 9 | 9 | 9 | 8 | 8 | 9 | 9 |
| alopecurus myosuroides | 4 | 4 | 6 | 8 | 7 | 9 | 9 | 9 | 6 | 9 | 9 | 9 | 6 | 8 | 9 | 9 | 3 | 5 | 8 | 9 |
| bromus tectorum | 7 | 8 | 8 | 9 | 8 | 9 | 9 | 9 | 8 | 9 | 9 | 9 | 9 | 9 | 9 | 9 | 7 | 8 | 9 | 9 |
| cyperus esculentus | 6 | — | 7 | — | 6 | 7 | 8 | 9 | 4 | — | 9 | — | 6 | — | 9 | — | 6 | — | 9 | — |
| rottboellia exaltata | 4 | 4 | 7 | 8 | 4 | 6 | 7 | 7 | 6 | 7 | 7 | 9 | 7 | 7 | 9 | 9 | 4 | 4 | 7 | 7 |
| digitaria sanguinalis | 4 | 6 | 7 | 9 | 6 | 7 | 9 | 9 | 3 | 8 | 9 | 9 | 8 | 8 | 9 | 9 | 5 | 6 | 7 | 8 |
| setaria italica | 2 | 6 | 6 | 8 | 4 | 8 | 9 | 9 | 3 | 8 | 9 | 9 | 4 | 7 | 9 | 9 | 8 | 9 | 9 | 9 |
| echinochloa crus galli | 2 | 2 | 2 | 4 | 2 | 2 | 3 | 4 | 3 | 6 | 8 | 8 | 2 | 6 | 6 | 8 | 2 | 2 | 2 | 3 |
| beta vulgaris | 2 | 2 | 3 | 3 | 2 | 2 | 2 | 3 | 2 | 2 | 3 | 3 | 3 | 3 | 4 | 5 | 2 | 2 | 3 | 3 |
| sesbania exaltata | 2 | 2 | 2 | 2 | 2 | 2 | 2 | 2 | 1 | 1 | 2 | 2 | 2 | 2 | 2 | 4 | 2 | 2 | 2 | 2 |
| amaranthus retroflexus | 1 | 2 | 5 | 6 | 1 | 1 | 2 | 7 | 1 | 1 | 4 | 4 | 6 | 8 | 9 | 9 | 1 | 1 | 2 | 3 |
| sinapis alba | 2 | 2 | 2 | 2 | 1 | 2 | 2 | 2 | 3 | 4 | 4 | 5 | 2 | 2 | 4 | 4 | 2 | 2 | 2 | 3 |
| ipomoea purpurea | 1 | 1 | 2 | 2 | 1 | 2 | 3 | 3 | 1 | 2 | 3 | 6 | 1 | 2 | 6 | 6 | 1 | 1 | 3 | 3 |
| galium aparine | 1 | 1 | 1 | 2 | 1 | 1 | 1 | 2 | 1 | 2 | 3 | 4 | 2 | 2 | 3 | 3 | 1 | 1 | 2 | 2 |

Post-emergence test

| Compound No. | 6 | | | | 9 | | | | 13 | | | | 21 | | | | 27 | | | |
|---|---|---|---|---|---|---|---|---|---|---|---|---|---|---|---|---|---|---|---|---|
| Amount applied kg/hectare | 4 | 2 | 1 | ½ | 4 | 2 | 1 | ½ | 4 | 2 | 1 | ½ | 4 | 2 | 1 | ½ | 4 | 2 | 1 | ½ |
| pastinaca sativa | 3 | 3 | 4 | 4 | 3 | 4 | 4 | 6 | 6 | 6 | 6 | 7 | 7 | 9 | 9 | 9 | 3 | 4 | 5 | 7 |
| matricaria chamomille | 5 | 7 | 8 | 8 | 9 | 9 | 9 | 9 | 7 | 8 | 9 | 9 | 9 | 9 | 9 | 9 | 8 | 9 | 9 | 9 |
| sida spinosa | 3 | 3 | 6 | 7 | 4 | 4 | 4 | 6 | 2 | 3 | 3 | 7 | 6 | 9 | 9 | 9 | 4 | 4 | 4 | 4 |
| rumex sp. | 1 | 1 | 1 | 1 | 1 | 2 | 2 | 3 | 1 | 1 | 4 | 5 | 2 | 2 | 3 | 4 | 1 | 1 | 1 | 2 |
| chrysanthemum leucum | 4 | 4 | 4 | 4 | 2 | 6 | 6 | 7 | 5 | 6 | 6 | 7 | 2 | 7 | 7 | 8 | 3 | 3 | 4 | 5 |
| abutilon sp. | 2 | 2 | 2 | 3 | 2 | 3 | 3 | 4 | 2 | 6 | 8 | 9 | 3 | 3 | 7 | 8 | 2 | 3 | 3 | 4 |
| solanum nigrum | 2 | 2 | 2 | 2 | 1 | 2 | 2 | 2 | 3 | 4 | 4 | 5 | 2 | 2 | 4 | 4 | 1 | 1 | 2 | 2 |

Post-emergence test

| Compound No. | 34 | | | | 40 | | | | 42 | | | | A | | | |
|---|---|---|---|---|---|---|---|---|---|---|---|---|---|---|---|---|
| Amount applied kg/hectare | 4 | 2 | 1 | ½ | 4 | 2 | 1 | ½ | 4 | 2 | 1 | ½ | 4 | 2 | 1 | ½ |
| plant | | | | | | | | | | | | | | | | |
| barley | 8 | 8 | 9 | 9 | 8 | 9 | 9 | 9 | 7 | 8 | 8 | 9 | 4 | 4 | 4 | 6 |
| wheat | 9 | 9 | 9 | 9 | 8 | 9 | 9 | 9 | 9 | 9 | 9 | 9 | 4 | 4 | 5 | 6 |
| maize | 3 | 7 | 7 | 7 | 4 | 4 | 7 | 9 | 6 | 6 | 6 | 9 | 4 | 6 | 6 | 7 |
| millet | 5 | 5 | 7 | 8 | 4 | 4 | 9 | 9 | 6 | 6 | 6 | 9 | 2 | 3 | 4 | 5 |
| rice | 7 | 8 | 8 | 9 | 7 | 7 | 7 | 9 | 6 | 6 | 6 | 8 | 4 | 6 | 6 | 7 |
| soya bean | 1 | 1 | 2 | 2 | 2 | 2 | 3 | 3 | 2 | 2 | 2 | 3 | 1 | 1 | 1 | 1 |
| cotton | 3 | 4 | 5 | 6 | 2 | 2 | 2 | 4 | 5 | 5 | 5 | 7 | 1 | 1 | 1 | 1 |
| avena fatua | 8 | 9 | 9 | 9 | 8 | 9 | 9 | 9 | 9 | 9 | 9 | 9 | 5 | 5 | 6 | 7 |
| lolium perenne | 8 | 9 | 9 | 9 | 9 | 9 | 9 | 9 | 9 | 9 | 9 | 9 | 6 | 7 | 7 | 8 |
| alopecurus myosuroides | 7 | 8 | 9 | 9 | 7 | 8 | 9 | 9 | 2 | 2 | 3 | 6 | 4 | 5 | 6 | 7 |
| bromus tectorum | 7 | 9 | 9 | 9 | 8 | 8 | 9 | 9 | 7 | 8 | 9 | 9 | — | — | — | — |
| cyperus esculentus | 3 | — | 5 | — | 4 | — | 8 | — | 4 | 7 | 9 | 9 | 8 | — | 9 | — |
| rottboellia exaltata | 5 | 6 | 7 | 7 | 7 | 8 | 8 | 9 | 5 | 7 | 8 | 9 | 2 | 3 | 4 | 5 |
| digitaria sanguinalis | 5 | 7 | 9 | 9 | 7 | 7 | 9 | 9 | 6 | 6 | 9 | 9 | 4 | 6 | 7 | 8 |
| setaria italica | 3 | 8 | 9 | 9 | 6 | 8 | 9 | 9 | 5 | 5 | 9 | 9 | 2 | 3 | 6 | 7 |
| echinochloa crus galli | 3 | 5 | 7 | 7 | 3 | 4 | 7 | 9 | 3 | 3 | 4 | 6 | 4 | 4 | 5 | 7 |
| beta vulgaris | 1 | 2 | 2 | 4 | 3 | 4 | 4 | 4 | 2 | 2 | 2 | 2 | 2 | 2 | 2 | 2 |
| sesbania exaltata | 1 | 1 | 1 | 2 | 2 | 2 | 2 | 2 | 2 | 2 | 2 | 2 | 1 | 1 | 1 | 2 |
| amaranthus retroflexus | 1 | 3 | 4 | 8 | 2 | 3 | 7 | 8 | 4 | 4 | 7 | 8 | 2 | 2 | 3 | 4 |
| sinapis alba | 2 | 2 | 3 | 4 | 2 | 2 | 2 | 4 | 2 | 2 | 2 | 3 | 2 | 2 | 2 | 3 |
| ipomoea purpurea | 1 | 2 | 3 | 5 | 2 | 2 | 2 | 4 | 1 | 1 | 3 | 3 | 1 | 1 | 1 | 2 |
| galium aparine | 1 | 1 | 2 | 3 | 1 | 1 | 2 | 2 | 1 | 1 | 1 | 2 | 1 | 1 | 1 | 1 |
| pastinaca sativa | 4 | 5 | 8 | 8 | 4 | 6 | 7 | 9 | 7 | 8 | 9 | 9 | 1 | 1 | 1 | 1 |
| matricaria chamomille | 7 | 7 | 9 | 9 | 8 | 9 | 9 | 9 | 7 | 7 | 9 | 9 | 1 | 2 | 3 | 3 |
| sida spinosa | 5 | 5 | 8 | 9 | 6 | 6 | 8 | 9 | 4 | 6 | 9 | 9 | — | — | — | — |
| rumex sp. | 1 | 1 | 1 | 2 | 1 | 1 | 1 | 2 | 2 | 2 | 2 | 4 | — | — | — | — |
| chrysanthemum leucum | 4 | 5 | 5 | 8 | 6 | 6 | 7 | 8 | 4 | 4 | 5 | 7 | — | — | — | — |
| abutilon sp. | 3 | 3 | 3 | 3 | 3 | 3 | 3 | 4 | 3 | 4 | 4 | 5 | — | — | — | — |
| solanum nigrum | 1 | 2 | 2 | 3 | 1 | 2 | 2 | 2 | 1 | 1 | 2 | 2 | — | — | — | — |

EXAMPLE 4

Field Test

Pre-emergence treatment

A field was sown at the beginning of March with spring wheat of the "Tano" variety and at the same time divided up into plots measuring 2 × 2 m. On the following day, the plots were treated with active-substance liquors produced from a 25% wettable powder by dilution with water, the treatment being such that amounts of active substance equivalent to 0.5, 1, 2 and 4 kg per hectare were sprayed onto the plots. Each concentration of active substance was tested on 4 different plots. Some plots were left untreated to serve as control plots. The test results were evaluated in May, after 69 days, when the wheat was about 25 cm high. The active substance used was 2-[(3,5-dichloro-6-methyl)-2-pyridyloxy]-propionic acid ethyl ester according to Example 1.

The evaluation of the condition of the cultivated plant and of the main weeds which had emerged in the natural way was made on the basis of the following scale of values.

1 plants thrive normally, as the untreated control plants, 2-3 slight damage,
4-6 moderate permanent damage,
7-8 severe damage,
9 plants destroyed.

The results are summarised in the following Table:

| Compound Amount applied kg/hectare | Example 1 | | | | none |
|---|---|---|---|---|---|
| | 0.5 | 1 | 2 | 4 | 0 |
| plants | | | | | |
| spring wheat "Tano" | 9 | 9 | 8 | 6 | 9 |
| Galium aparine | 1 | 1 | 1 | 1 | 9 |
| Sinapis alba | 7 | 3 | 3 | 9 | 9 |
| Chenopodium album | 1 | 1 | 1 | 1 | 9 |

The control plots were covered to the extent of 5% with weeds.

Post-emergence treatment

A field sown with winter wheat of the "Svenno" variety was divided in May, when the wheat stood several cm high and the weeds had just emerged and were in the 2-4 leaf stage, into plots measuring 2 × 2 meters. These were then treated with an active-substance liquor in such a manner that amounts of active substance equivalent to 0.5, 1, 2 and 4 kg per hectare were applied to the plots. Each concentration of active substance was tested on 4 plots; some plots remained untreated to serve as control plots. The test was evaluated in June, after 90 days, when the wheat was 40-50 cm high and the weeds 20-30 cm high, and shortly before blossoming.

The active substance of Example 1 was compared with 4-amino-3,5,6-trichloropicolinic acid (A), known from Science 141, 363 (1963) or from U.S. Pat. No. 3,234,229. The evaluation was made according to the given scale of values. The results are summarised in the following Table:

| Compound Amount applied kg/hectare | none | 1 | | | | | A | | |
|---|---|---|---|---|---|---|---|---|---|
| | 0 | ½ | 1 | 2 | 4 | ½ | 1 | 2 | 4 |
| plant | | | | | | | | | |
| spring wheat "Svenno" | 9 | 9 | 9 | 9 | 9 | 9 | 9 | 8 | 3 |
| Galium aparine | 9 | 5 | 4 | 3 | 2 | 4 | 2 | 2 | 2 |
| Chenopodium album | 9 | 6 | 2 | 1 | 1 | 2 | 2 | 2 | 2 |
| Capsiella bursa pastoris | 9 | 6 | 2 | 1 | 1 | 2 | 8 | 8 | 8 |
| % overgrown with weeds | 80% | 25% | 10% | 5% | 3% | 30% | 20% | 20% | 5% |

For the purpose of application in agriculture, these compounds are advantageously formulated as a herbicidal composition, and applied in amounts of between 0.1 and 10 kg of active substance per hectare, preferably between 0.2 and 5 kg per hectare. The active substances are formulated together with one or more carrier substances, emulsifiers and other additives. Such accompanying substances can be solid or liquid. It is possible to use solvents, diluents, dispersing agents, wetting agents, adhesives, thickeners or binding agents.

The compositions are accordingly formulated as emulsion or suspension concentrates, wettable powders, dusts, scattering agents or granulates.

The sprayable solutions for direct use contain, for example, mineral oil fractions of high to medium boiling range, especially above 100° C, such as diesel oil or kerosene, also coal-tar oil or vegetable or animal oils, as well as hydrocarbons, e.g. alkylated naphthalenes, tetrahydronaphthalene, xylene mixtures, cyclohexanols and, optionally, also ketones, chlorinated hydrocarbons such as tetrachloroethane, trichloroethylene or tri- and tetrachlorobenzenes.

For application in an aqueous form, there are used emulsion concentrates, pastes or wettable powders, with the addition of water. Suitable emulsifiers or dispersing agents are nonionic products, e.g. condensation products of aliphatic alcohols, amines or carboxylic acids having a long-chain hydrocarbon radical of about 10 to 30 carbon atoms with ethylene oxide, such as the condensation product of octadecyl alcohol and 25 to 30 moles of ethylene oxide, or that of soybean fatty acid and 30 moles of ethylene oxide, or that of commercial oleylamine and 15 moles of ethylene oxide, or that of dodecylmercaptan and 12 moles of ethylene oxide. It is also possible to use however condensation products of ethylene oxide with hydroaromatic polycyclic carboxylic acids or amines. Among the anion-active emulsifiers which can be employed, there may be mentioned: the sodium salt of the dodecyl alcohol sulphuric acid ester, the sodium salt of dodecylbenzenesulphonic acid, the potassium or triethanolamine salt of oleic acid or of abietic acid or of mixtures of these acids, or the sodium salt of a petroleum-sulphonic acid. Suitable cation-active dispersing agents are quaternary ammonium and phosphonium compounds, such as cetylpyridinium chloride or the dioxyethylbenzyldodecylammonium chloride.

If the novel compositions are used in the form of dusts or scattering agents, they can contain as solid carriers: talcum, kaolin, bentonite, sand, calcium carbonate or calcium phosphate; also charcoal, cork flour and wood flour, and other materials of vegetable origin.

Dusts having a content of 5-10% of the active compound can be produced by dilution of a wettable powder with a finely divided solid carrier. Wetting agents and dispersing agents can also be dispensed with or replaced by others. The various preparations can contain in the customary manner an addition of substances which improve the dispersion, adhesiveness or penetration capacity; such substances which may be mentioned are fatty acids, resins, glue, casein or, e.g., alginate.

The use of granulates has proved very advantageous for combating weeds in rice crops, particularly in wet paddy rice.

Such granulates can be produced by dissolving the active-substance mixture in an organic solvent, and applying the solution obtained to a granulated mineral, e.g. to attapulgite, $SiO_2$, granicalcium, bentonite, etc., and subsequently removing the organic solvent by evaporation.

It is also possible to use polymer granulates. These can be produced by mixing the active substances with polymerisable compounds (urea/formaldehyde, dicyanodiamide/formaldehyde, melamine/formaldehyde or others), whereupon a careful polymerisation is performed which leaves the active substances unaffected, with granulation being carried out actually as gel formation is occurring. It is however more advantageous to impregnate finished porous polymer granulates (urea/formaldehyde, polyacrylonitrile, polyester and so forth) having a specific surface area and a favourable predeterminable adsorption/desorption ratio with the active substances, e.g. in the form of their solutions (in a low-boiling solvent), and to subsequently remove the solvent.

Such polymer granulates can be applied in the form of microgranules having bulk weights preferably of 300 g/liter to 600 g/liter with the aid of atomisers. The atomising can be carried out over extensive areas with the use of aeroplanes.

It is obviously possible to add to the granulates, e.g., fertilisers, surface-active agents, or substances for increasing the specific weight, such as $BaSO_4$.

Granulates are also obtainable by compacting the carrier materials with the active substances and additives and subsequently pulverising the compacted material.

The concentration of active substance in the herbicidal compositions is 0.1–95 per cent by weight, preferably 5–85 per cent by weight.

FORMULATION EXAMPLES

Wettable Powder

The following constituents are mixed together and finely ground to produce a water-soluble wettable powder:
50 parts of active substance according to the present invention,
20 parts of Hisil (highly adsorptive silicic acid),
25 parts of bolus alba (kaolin),
1.5 parts of 1-benzyl-2-stearyl-benzimidazole-6,3'-disulphonate,
3.5 parts of the reaction product from p-tert.-octylphenol and ethylene oxide.

Emulsion Concentrates (a) 40 Parts of an active substance of the formula I are mixed with 10 parts of a mixture of an anionic surface-active compound, preferably the calcium or magnesium salt of monolauryl-benzene-monosulphonic acid, and a nonionic surface-active compound, preferably a polyethylene glycol ether of monosorbitol-laureate, and the whole is dissolved in a small amount of xylene. The amount is made up with xylene to 100 ml to give a clear solution; this can be used as a wettable-powder concentrate, which can be poured into water to obtain a stable emulsion.

(b) Readily soluble active substances can be formulated as an emulsion concentrate also by the following method:
20 parts of an active-substance mixture,
70 parts of xylene, and
10 parts of a mixture of a reaction product of an alkyl-phenol with ethylene oxide and calcium decylbenzene sulphonate
are mixed together. A sprayable emulsion is formed by dilution with water to the desired concentration.

Granulates (a) 7.5 g of an active substance of the formula I is dissolved in 100 ml of acetone, and the acetone solution thus obtained is applied to 92 g of granulated attapulgite (size of mesh: 24/48 mesh/inch). The whole is well mixed and the solvent is evaporated off in a rotary evaporator to give a granulate having a content of active substance of 7.5%.

(b) To produce a 10% polymer granulate, 1050 to 1100 g of commercial active substance is dissolved in 2 liters of trichloroethylene, and the solution is sprayed in a fluidisation granulator, at a spray pressure of 1.5 atm. (excess pressure) onto 9230 g of porous urea/formaldehyde granulate. The solvent can be removed by heating the air spirals to about 50° C.

(c) A 7.5% weighted granulate is produced by pressing 770 g of a solid commercial active substance, 500 g of $BaSO_4$, 100 g of urea and 7730 g of pulverulent porous polyacrylonitrile in a roll mill, and subsequently reducing the resulting material to the desired particle size.

What is claimed is:
1. A 2-Pyridinol compound of the formula I

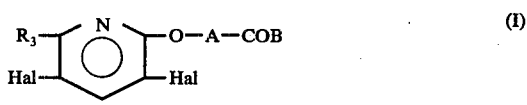

wherein
A represents an alkylene bridge member having 1–9 C atoms, which can be branched-chain or straight-chain and which can be substituted by halogen;
B represents a group $-OR_1$ or $-SR_2$ in which
$R_1$ represents hydrogen; $C_1-C_8$ alkyl which is unsubstituted or substituted by halogen, $C_1-C_4$ alkoxy, $C_1-C_4$ alkylthio, $C_1-C_4$ alkoxycarbonyl, $C_3-C_{12}$ cycloalkyl, phenyl which is unsubstituted or mono- or polysubstituted by halogen, $C_1-C_4$ alkyl, $C_1-C_4$ alkoxy, $C_1-C_4$ alkylthio, cyano or nitro; $C_3-C_{12}$ cycloalkyl; $C_3-C_8$ alkenyl which is unsubstituted or substituted by halogen; $C_3-C_8$ alkynyl; phenyl which is unsubstituted or mono- or poly-substituted by halogen, $C_1-C_4$ alkyl, $C_1-C_4$ alkoxy, $C_1-C_4$ alkylthio, cyano or nitro; an ion equivalent of an alkali metal atom; or a quaternary $C_1-C_4$ alkylammonium group or $C_1-C_4$ hydroxyalkyl-ammonium group; and
$R_2$ represents $C_1-C_8$ alkyl, a phenyl or benzyl group which can be unsubstituted or substituted by halogen, $C_1-C_4$ alkyl or $C_1-C_4$ alkoxy;
$R_3$ represents $C_1-C_4$ alkyl or phenyl; and Hal independently represent a chlorine or bromine atom.

2. 2-[(3,5,-Dichloro-6-methyl)-2-pyridyloxy]-propionic acid ethyl ester according to claim 1.

3. 2-[(3,5-Dichloro-6-methyl)-2-pyridyloxy]-propionic acid according to claim 1.

4. 2-[3,5-dichloro-6-methyl)-2-pyridyloxy] acetic acid methyl enter according to claim 1.

5. Sodium salt of 2-[(3,5-dichloro-6-methyl)-2-pyridyloxy]-propionic acid according to claim 1.

6. (Di-hydroxyethyl) ammonium salt of 2-[(3,5-dichloro-6-methyl)-2-pyridyloxy]-propionic acid according to claim 1.

7. 2-[(3,5,-dichloro-6-methyl)-2-pyridyloxy]-propionic acid isobutyl ester according to claim 1.

8. 2-[(3,5-dichloro-6-methyl)-2-pyridyloxy]-propionic acid heptynyl-3 ester according to claim 1.

9. 2-[(3,5-dichloro-6-methyl)-2-pyridyloxy]-propionic acid butoxyethyl ester accordings to claim 1.

10. 2-[(3,5-dichloro-6-methyl)-2-pyridyloxy]-propionic acid cyclohexyl ester according to claim 1.

11. A herbicidal composition for the selective control of weeds and wild grasses in crops of useful plants, which composition contains as active substance a herbicidally effective amount of a 2-pyridinol compound corresponding to the formula I, claim 1, together with a suitable carrier therefor.

12. A method for the selective control of weeds and wild grasses in crops of useful plants which comprises applying to the areas where said crop is or is to be grown a herbicidally effective amount of a compound of formula I, claim 1.

* * * * *